(12) United States Patent
Kuhn et al.

(10) Patent No.: US 8,352,008 B2
(45) Date of Patent: Jan. 8, 2013

(54) ACTIVE NOISE CANCELLATION IN AN OPTICAL SENSOR SIGNAL

(75) Inventors: Jonathan L. Kuhn, Ham Lake, MN (US); David A. Anderson, Stanchfield, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 349 days.

(21) Appl. No.: 12/797,831

(22) Filed: Jun. 10, 2010

(65) Prior Publication Data

US 2010/0317943 A1 Dec. 16, 2010

Related U.S. Application Data

(60) Provisional application No. 61/185,838, filed on Jun. 10, 2009.

(51) Int. Cl.
*A61B 5/00* (2006.01)
(52) U.S. Cl. .......................................... 600/336
(58) Field of Classification Search .................. 600/336
See application file for complete search history.

(56) References Cited

U.S. PATENT DOCUMENTS

| | | | |
|---|---|---|---|
| 4,180,078 A | 12/1979 | Anderson | |
| 4,202,339 A | 5/1980 | Wirtzfeld et al. | |
| 4,230,122 A | 10/1980 | Lubbers et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Picchi et al. | |
| 4,750,495 A | 6/1988 | Moore et al. | |
| 4,967,748 A | 11/1990 | Cohen | |
| 5,007,423 A | 4/1991 | Branstetter et al. | |
| 5,163,427 A | 11/1992 | Keimel | |
| 5,176,137 A | 1/1993 | Erickson et al. | |
| 5,188,105 A | 2/1993 | Keimel | |
| 5,188,108 A | 2/1993 | Secker | |
| 5,193,535 A | 3/1993 | Bardy et al. | |
| 5,213,098 A | 5/1993 | Bennett | |

(Continued)

FOREIGN PATENT DOCUMENTS

EP   760476   3/1997

(Continued)

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 034017 (May/Jun. 2005).

(Continued)

*Primary Examiner* — W. B. Perkey
(74) *Attorney, Agent, or Firm* — Evans M. Mburu; Michael C. Soldner; Stephen W. Bauer

(57) ABSTRACT

A medical device system and associated method are used for monitoring tissue oxygenation. An optical sensor produces a signal corresponding to tissue light attenuation. A processor receives the optical sensor signal and computes a first measure of light attenuation at a first light wavelength and a second measure of light attenuation at a second light wavelength. In one embodiment, noise cancellation circuitry receives the first measure and the second measure and generates a guessed ratio of the first and second measures. Using the first measure, the second measure and the guessed ratio, the noise cancellation circuitry provides a peak output power when the guessed ratio corresponds to an actual ratio of the first and second measures.

25 Claims, 7 Drawing Sheets

U.S. PATENT DOCUMENTS

| | | | |
|---|---|---|---|
| 5,218,962 A | 6/1993 | Mannheimer et al. | |
| 5,227,181 A | 7/1993 | Knudsen | |
| 5,354,316 A | 10/1994 | Keimel | |
| 5,364,316 A | 11/1994 | Brambilla | |
| 5,385,143 A | 1/1995 | Aoyagi | |
| 5,398,680 A | 3/1995 | Polson et al. | |
| 5,431,172 A | 7/1995 | Hoegnelid et al. | |
| 5,464,434 A | 11/1995 | Alt | |
| 5,470,345 A | 11/1995 | Hassler et al. | |
| 5,531,714 A | 7/1996 | Dahn et al. | |
| 5,545,186 A | 8/1996 | Olson et al. | |
| 5,588,427 A * | 12/1996 | Tien | 600/323 |
| 5,593,431 A | 1/1997 | Sheldon | |
| 5,596,986 A | 1/1997 | Goldfarb | |
| 5,683,432 A | 11/1997 | Goedeke et al. | |
| 5,725,219 A | 3/1998 | Gilbert | |
| 5,752,519 A | 5/1998 | Benaron et al. | |
| 5,769,785 A * | 6/1998 | Diab et al. | 600/364 |
| 5,855,593 A | 1/1999 | Olson et al. | |
| 5,879,294 A | 3/1999 | Anderson et al. | |
| 5,902,326 A | 5/1999 | Lessar et al. | |
| 6,144,866 A | 11/2000 | Miesel et al. | |
| 6,198,952 B1 | 3/2001 | Miesel et al. | |
| 6,226,540 B1 | 5/2001 | Bernreuter | |
| 6,236,882 B1 | 5/2001 | Lee et al. | |
| 6,292,698 B1 | 9/2001 | Duffin et al. | |
| 6,377,840 B1 | 4/2002 | Gritsenko et al. | |
| 6,473,632 B1 | 10/2002 | Myers | |
| 6,481,899 B1 | 11/2002 | Quast et al. | |
| 6,487,343 B1 | 11/2002 | Lewandowski et al. | |
| 6,512,940 B1 | 1/2003 | Brabec et al. | |
| 6,522,915 B1 | 2/2003 | Ceballos et al. | |
| 6,599,250 B2 | 7/2003 | Webb et al. | |
| 6,615,064 B1 | 9/2003 | Aldrich | |
| 6,622,046 B2 | 9/2003 | Fraley et al. | |
| 6,667,803 B1 | 12/2003 | Flessland et al. | |
| 6,682,135 B2 | 1/2004 | Zheng | |
| 6,738,667 B2 | 5/2004 | Deno et al. | |
| 6,839,583 B1 | 1/2005 | Lewandowski et al. | |
| 6,839,592 B2 | 1/2005 | Grandjean | |
| 6,850,787 B2 * | 2/2005 | Weber et al. | 600/323 |
| 6,892,006 B2 | 5/2005 | Lewandowski et al. | |
| 6,944,488 B2 | 9/2005 | Roberts | |
| 6,997,879 B1 | 2/2006 | Turcott | |
| 7,043,294 B1 | 5/2006 | Paris | |
| 7,096,064 B2 | 8/2006 | Deno et al. | |
| 7,164,948 B2 | 1/2007 | Struble et al. | |
| 7,165,893 B2 | 1/2007 | Schmitz | |
| 7,177,686 B1 | 2/2007 | Turcott | |
| 7,239,385 B2 | 7/2007 | Schmitz et al. | |
| 7,239,901 B2 | 7/2007 | Gritsenko | |
| 7,277,757 B2 | 10/2007 | Casavant et al. | |
| 7,302,294 B2 | 11/2007 | Kamath et al. | |
| 7,809,441 B2 | 10/2010 | Kane et al. | |
| 7,991,448 B2 * | 8/2011 | Edgar et al. | 600/336 |
| 8,038,626 B2 | 10/2011 | Cinbis et al. | |
| 8,055,321 B2 | 11/2011 | Bernreuter | |
| 8,090,432 B2 | 1/2012 | Cinbis et al. | |
| 8,165,662 B2 | 4/2012 | Cinbis et al. | |
| 2003/0004412 A1 | 1/2003 | Izatt et al. | |
| 2003/0144584 A1 | 7/2003 | Mendelson | |
| 2003/0187480 A1 | 10/2003 | KenKnight et al. | |
| 2003/0199956 A1 | 10/2003 | Strubble | |
| 2004/0024297 A1 | 2/2004 | Chen et al. | |
| 2004/0220629 A1 | 11/2004 | Kamath et al. | |
| 2005/0119586 A1 | 6/2005 | Coyle et al. | |
| 2005/0148832 A1 | 7/2005 | Reghabi et al. | |
| 2005/0277818 A1 | 12/2005 | Myers | |
| 2006/0009685 A1 | 1/2006 | Finarov et al. | |
| 2006/0106293 A1 | 5/2006 | Fantini | |
| 2006/0253007 A1 | 11/2006 | Cheng et al. | |
| 2007/0239052 A1 | 10/2007 | Bhunia | |
| 2007/0239053 A1 | 10/2007 | Bhunia | |
| 2007/0239215 A1 | 10/2007 | Bhunia et al. | |
| 2007/0255148 A1 | 11/2007 | Bhunia | |
| 2008/0004513 A1 | 1/2008 | Walker et al. | |
| 2008/0015424 A1 | 1/2008 | Bernreuter | |
| 2008/0103538 A1 | 5/2008 | Walker et al. | |
| 2008/0208020 A1 | 8/2008 | Cinbis | |
| 2008/0208269 A1 | 8/2008 | Cinbis et al. | |
| 2008/0306390 A1 | 12/2008 | Cinbis | |
| 2010/0185252 A1 | 7/2010 | Bjorling et al. | |
| 2010/0292548 A1 | 11/2010 | Baker, Jr. et al. | |
| 2010/0317943 A1 * | 12/2010 | Kuhn et al. | 600/323 |
| 2011/0066017 A1 | 3/2011 | Kuhn | |

FOREIGN PATENT DOCUMENTS

| | | |
|---|---|---|
| EP | 1764034 | 3/2007 |
| EP | 1955653 | 8/2008 |
| GB | 1419701 | 12/1975 |
| WO | 9825669 | 6/1998 |
| WO | 03077750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | 2008151263 | 12/2008 |

OTHER PUBLICATIONS

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305.

St Jude Medical, ME 317: Design for Manufacturability, Implantable Pulse Generator Optical Sensing System, Jun. 1, 2004, 225 pages.

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

JR Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

\* cited by examiner

US 8,352,008 B2

ACTIVE NOISE CANCELLATION IN AN OPTICAL SENSOR SIGNAL

RELATED PRIORITY APPLICATION

The present application claims priority and other benefits from U.S. Provisional Patent Application Ser. No. 61/185,838, filed Jun. 10, 2009, entitled "ACTIVE NOISE CANCELLATION IN AN OPTICAL SENSOR SIGNAL", incorporated herein by reference in it's entirety.

REFERENCE TO RELATED APPLICATIONS

Cross-reference is hereby made to the commonly-assigned related U.S. Applications: Ser. Nos. 12/797,736, 12/797,744 and 12/797,770, all entitled "DEVICE AND METHOD FOR MONITORING ABSOLUTE OXYGEN SATURATION AND TOTAL HEMOGLOBIN CONCENTRATION", to Kuhn et al.; Ser. Nos. 12/797,815, 12/797,816 and 12/797,823, all entitled "TISSUE OXYGENATION MONITORING IN HEART FAILURE" to Cinbis et al. Ser. Nos. 12/797,781 and 12/797,793, both entitled "SHOCK REDUCTION USING ABSOLUTE CALIBRATED TISSUE OXYGEN SATURATION AND TOTAL HEMOGLOBIN VOLUME FRACTION", to Kuhn et al.; and Ser. Nos. 12/797,800 and 12/797,811, both entitled "ABSOLUTE CALIBRATED TISSUE OXYGEN SATURATION AND TOTAL HEMOGLOBIN VOLUME FRACTION", to Kuhn et al., all of which are incorporated herein by reference in their entireties.

TECHNICAL FIELD

The disclosure relates generally to medical devices and, in particular, to a medical device including an optical sensor for measuring tissue oxygenation and an associated method for cancelling noise in an optical sensor signal.

BACKGROUND

Optical sensors can be used for monitoring oxygenation of blood or tissue. Optical sensor signals tend to be sensitive to motion because movement of the sensor alters the optical pathway of the sensor through a volume of tissue adjacent to the sensor. Measurements using optical sensors are particularly susceptible to motion artifact when the adjacent tissue is not a uniform, homogeneous tissue. Motion sensitivity of optical sensors makes monitoring of tissue oxygenation in a patient challenging, particularly in an ambulatory patient. However, tissue oxygenation monitoring can provide valuable data for use in diagnosing a patient condition and managing a therapy. A need remains for medical devices including optical sensors and associated methods for reliably monitoring tissue oxygenation in the presence of motion or other noise sources.

DETAILED DESCRIPTION

Figure 1:
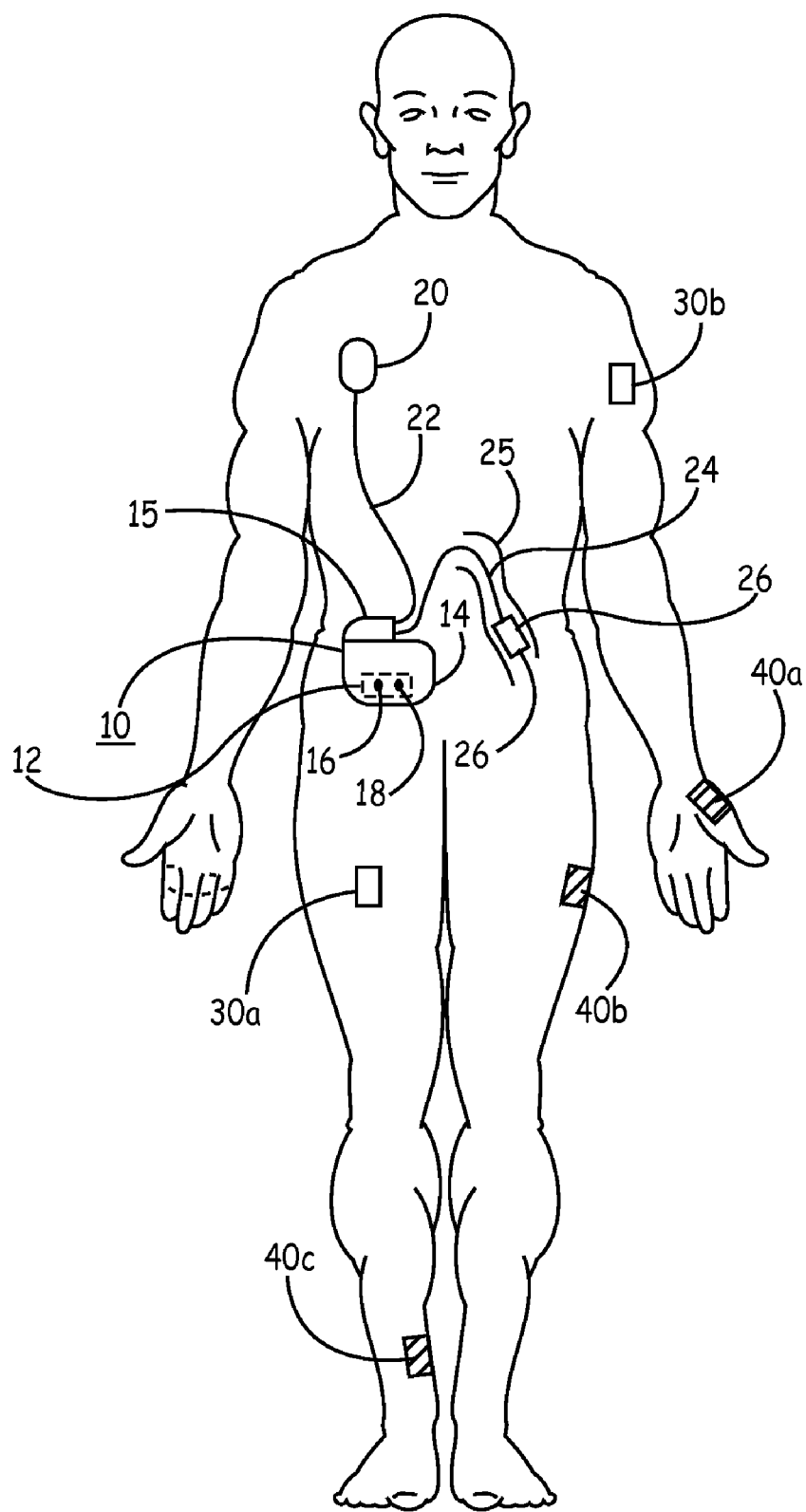
FIG. 1 is a schematic view of a medical device system for monitoring tissue oxygenation in a patient.

In the following description, references are made to illustrative embodiments. It is understood that other embodiments may be utilized without departing from the scope of the disclosure. In some instances, for purposes of clarity, for example, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments described herein, an optical sensor is used to monitor tissue oxygenation in a measurement tissue volume. The measurement volume is the volume of tissue (including blood) in the optical path of the sensor. The term "tissue oxygenation" as used herein refers to the availability of oxygen to a localized tissue volume and thus refers generally to the availability of oxygenated hemoglobin. The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume. Generally speaking, when the availability of oxygen to a body tissue is being monitored, the measurement volume of the optical sensor preferably extends through a substantially uniform tissue volume such that optical sensor signals used to compute measurements of tissue oxygenation correlate to the absolute tissue oxygen saturation and HbT in the microcirculation within the measurement volume.

Absolute tissue oxygen saturation ($O_2$Sat) is the portion (or percentage) of the total hemoglobin that is in an oxygenated state. More specifically, $O_2$Sat relates to the hemoglobin binding sites holding an oxygen molecule. Thus, "tissue oxygenation monitoring" as used herein refers to monitoring both $O_2$Sat (or an index thereof) and HbT (or an index thereof). Tissue oxygenation monitoring may involve determining absolute measurements of $O_2$Sat and HbT or determining trends of these measurements or trends of indices of these measurements. When either $O_2$Sat or HbT are reduced, a blood-perfused tissue can become hypoxic. The term "hypoxia" as used herein refers to a reduced availability of oxygen to the tissue.

Tissue oxygenation monitoring applications may include chronic or acute monitoring of tissue oxygenation using an implantable or external medical device including an optical sensor. As used herein, "chronic" monitoring generally refers to monitoring a tissue for more than one day using continuous or periodic measurements while "acute" monitoring generally refers to monitoring a tissue for one day or less, for example, testing performed during a clinical visit or measurements performed during a surgical procedure.

FIG. 1 is a schematic drawing of an implantable medical device (IMD) 10 configured for monitoring tissue oxygenation in a patient. IMD 10 may be embodied as any of a number of implantable medical devices, including pacemakers, implantable cardioverter defibrillators (ICDs), nerve stimulators, fluid delivery pumps, hemodynamic monitors, ECG monitors, or the like. In one embodiment, IMD 10 includes an optical sensor 12 incorporated in hermetically-sealed housing 14 of IMD 10. Housing 14 encloses an IMD battery and other device circuitry and components and includes at least one opening or window 16 through which light is emitted from a light emitting portion of the optical sensor 12 and at least one additional window 18 through which light is detected by a light detecting portion of optical sensor 12.

It is recognized that in sensor 12, and any of the other sensor embodiments described herein, multiple windows may be provided to allow multiple light emitting and/or light detecting portions to be selected in different combinations for performing oxygenation measurements, which may include using emitting and detecting portions at different distances apart. The distance between the emitting and detecting portion determines, in part, the optical pathway of the sensor and thus the measurement volume and depth. Therefore, selection of different emitting and detecting portions and different emitting-to-detecting spacings allows oxygenation measurements to be performed in different measurement volumes in tissue adjacent to the sensor.

In some embodiments, an optical sensor 20 may be carried by a lead 22 extending from IMD 10. Lead 22 is coupled to circuitry within housing 14 via a connector block 15 including appropriate electrical connections and feedthroughs to allow circuitry within housing 14 to be coupled to sensor 20. A lead 22 may be used to deploy sensor 20 at a tissue site remote from the implant site of IMD 10. Lead 22 may be tunneled extravascularly, e.g., subcutaneously or sub-muscularly, to a desired monitoring site.

In alternative embodiments, a lead 24 carrying an optical sensor 26 near or at a distal end of the lead 24, may be advanced within the vascular system and remain within a blood vessel 25 for measuring O$_2$Sat and HbT within the blood stream or in tissue adjacent to blood vessel 25. Alternatively, lead 24 may be advanced intravascularly to a desired tissue site then advanced through the vessel wall, for example by puncturing the vessel wall, for placement at an adjacent tissue site.

Sensors 30a and 30b are shown as implantable, wireless optical sensors including a telemetry module (not shown) enabled for wireless communication with IMD 10 or an external medical device, such as a bedside monitor, home monitor or device programmer. A wireless sensor 30a or 30b may be implanted at a desired monitoring site remote from IMD 10 without the surgical constraints imposed by tethering sensor 30A or 30B to IMD 10 using a conductive lead. A leadless sensor 30a or 30b may be implanted for monitoring purposes only, without added therapy delivery capabilities, and may be used alone or in conjunction with another IMD 10.

In other embodiments, an external, wearable optical sensor 40a, 40b, or 40c, collectively referred to as 40, may be provided for ambulatory, chronic or acute monitoring of tissue. Examples of placement of an external optical sensor 40 at different monitoring sites is illustrated in FIG. 1, which may be any external site including core body locations or the extremities. For example, external optical sensors 40 may include a sensor 40a placed along the thenar muscle (along the palm of the hand just beneath the thumb), a sensor 40b along the upper leg, or a sensor 40c along the lower leg or foot. External sensors 40 may be held in a stable position using an adhesive patch or tape or using a securable band or cuff.

Figure 2:
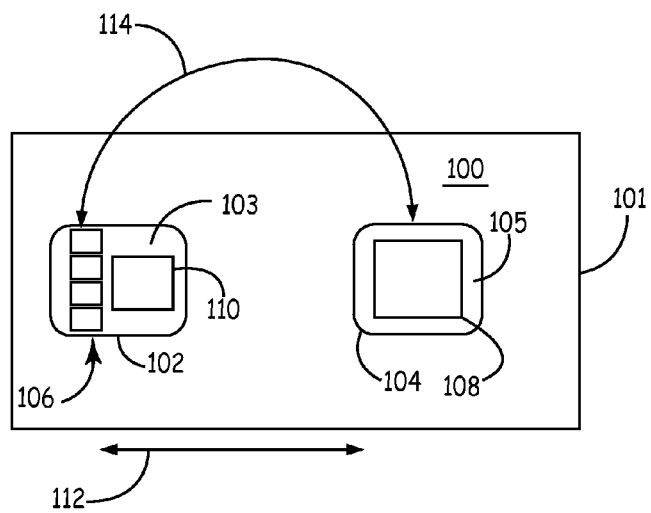
FIG. 2 is a top, schematic view of an optical sensor according to one embodiment.

FIG. 2 is a top, schematic view of an optical sensor according to one embodiment. It is recognized that numerous optical sensor configurations may be used for monitoring tissue oxygenation, and the methods and devices described herein are not limited to a particular optical sensor configuration. In general, any optical sensor that acquires measurements of the attenuation of light in a tissue volume for computing a measurement correlated to tissue oxygenation may be used. In some embodiments, tissue oxygenation measurements may include a non-calibrated index of oxygen saturation determined using a two-wavelength optical sensor, typically emitting and detecting red and infrared light, as generally disclosed in U.S. Patent Application No. 2007/0255148 (Bhunia), hereby incorporated herein by reference in its entirety. In other embodiments, tissue oxygenation measurements may include non-calibrated indices of oxygen saturation and blood volume determined using a two-wavelength (typically red and infrared) optical sensor or a three-wavelength (typically red, isosbestic and infrared) optical sensor as generally described in U.S. Patent Publication No. 2008/0208269 (Cinbis, et al), hereby incorporated herein by reference in its entirety.

In the illustrative embodiments described herein, calibrated measures of O$_2$Sat and HbT are measured using a four wavelength optical sensor. Examples of optical sensors emitting and detecting at least four wavelengths are generally described in U.S. Pat. Appl. Ser. No. 61/185,818, (Kuhn et al., entitled "DEVICE AND METHOD FOR MONITORING ABSOLUTE OXYGEN SATURATION AND TOTAL HEMOGLOBIN CONCENTRATION", hereby incorporated herein by reference in its entirety. Second derivatives of attenuation spectra can be used to obtain a calibrated measurement O$_2$Sat and a calibrated measurement of HbT. Determination of absolute calibrated measures of O$_2$Sat and HbT allows tissue oxygenation at a particular time point to be evaluated as well as long term changes in tissue oxygenation (e.g. over minutes, hours, days or weeks) to be monitored. The use of non-calibrated indices of tissue oxygen saturation and blood volume available from 2- or 3-wavelength optical sensor devices allows relatively shorter term trends in tissue oxygenation (for example over seconds and possibly minutes) to be monitored. Both short-term monitoring of tissue oxygenation index trends and absolute value and long-term monitoring of calibrated measurements of tissue oxygenation can be useful in monitoring a patient and/or managing a therapy.

While illustrative embodiments described herein utilize 4-wavelengths of light attenuation measurements to obtain calibrated measurements or uncalibrated indices of O$_2$Sat and HbT, it is recognized that uncalibrated indices of tissue oxygenation measurements obtained from 2- or 3-wavelength optical sensor devices may be substituted when short-term trends are being evaluated for assessing tissue oxygenation.

Sensor 100 may generally correspond to sensor 12, 20, 30, 34 or 40 in FIG. 1. Sensor 100 includes a light emitting portion 102 and a light detecting portion 104. Light emitting portion 102 includes one or more light sources 106 positioned to emit light through a lens 103 sealed in an opening in hermetically-sealed housing 101. Light source(s) 106 may be embodied as single white light source or multiple light sources emitting light at separate spaced-apart wavelengths. Suitable light sources include, without limitation, optoelectronic devices such as light emitting diodes (LEDs), lasers such as vertical cavity surface emitting lasers (VCSELs), luminescent, phosphorescent or incandescent light sources. In one embodiment, light sources 106 are embodied as light emitting diodes (LEDs) emitting light in the visible, e.g. red, and/or infrared light spectrum.

For example, light sources 106 may include four LEDs in emitting portion 102 for emitting light at separate wavelengths of 680 nm, 720 nm, 760 nm, and 800 nm. Alternatively, four LEDs provided as light sources 106 may emit light at 660 nm, 720 nm, 760 nm, and 810 nm. In another embodiment, four LEDs are included emitting light at 720 nm, 760 nm, 810 nm, and 850 nm. In yet another embodiment, four LEDs are included that emit light at 720 nm, 760 nm, 810 nm, and 890 nm. Any combination of light sources emitting light at any of the wavelengths mentioned herein may be used. Furthermore, it is recognized that the specified wavelengths are approximate and each light source may emit a narrow band of light wavelengths which is approximately centered on, or at least includes, the specified wavelength. The light sources may be controlled to emit light sequentially or simultaneously.

In the embodiment shown, the light emitting portion 102 further includes a reference light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the materials encountered by light emitted by light sources 106 before entering an adjacent tissue volume, e.g. lens 103. Reference light detector 110 provides an output signal for measuring or detecting changes in the intensity of the light emitted by emitting portion 102.

The reference light detector 110 output signal can be used in computing or adjusting $O_2Sat$ and HbT measurements. Additionally or alternatively, an output signal from reference light detector 110 can be used as a feedback signal for controlling the drive signals applied to light sources 106 to cause light emission.

In other embodiments, a light detector 110 is not included in the emitting portion 102. The emitted light intensity is assumed to be stable throughout the usable life of the sensor so as not to introduce significant error in light attenuation measurements used for computing tissue $O_2Sat$ and HbT.

The light detecting portion 104 includes a light detector 108 positioned to receive light through a lens 105 mounted in an opening in housing 101. The light detector 108 may be embodied as a photodiode. Other components suitable for use as a light detector include a photoresistor, phototransistor, photovoltaic cell, photomultiplier tube, bolometer, charge-coupled device (CCD) or an LED reverse-biased to function as a photodiode. Light detector 108 receives light scattered by an adjacent tissue volume. The distance 112 between the light sources 106 and the light detector 108 will influence the optical path 114 (shown schematically) of sensor 100. Greater spacing (longer distance 112) between the emitting and detecting portions will result in a longer optical pathway 114, extending deeper in the adjacent tissue volume, than relatively shorter spacing between light sources 106 and light detector 108. As such, different spacing between emitting and detecting portions 102 and 104 will result in tissue oxygenation measurements relating to different depths of an adjacent body tissue.

Figure 3:
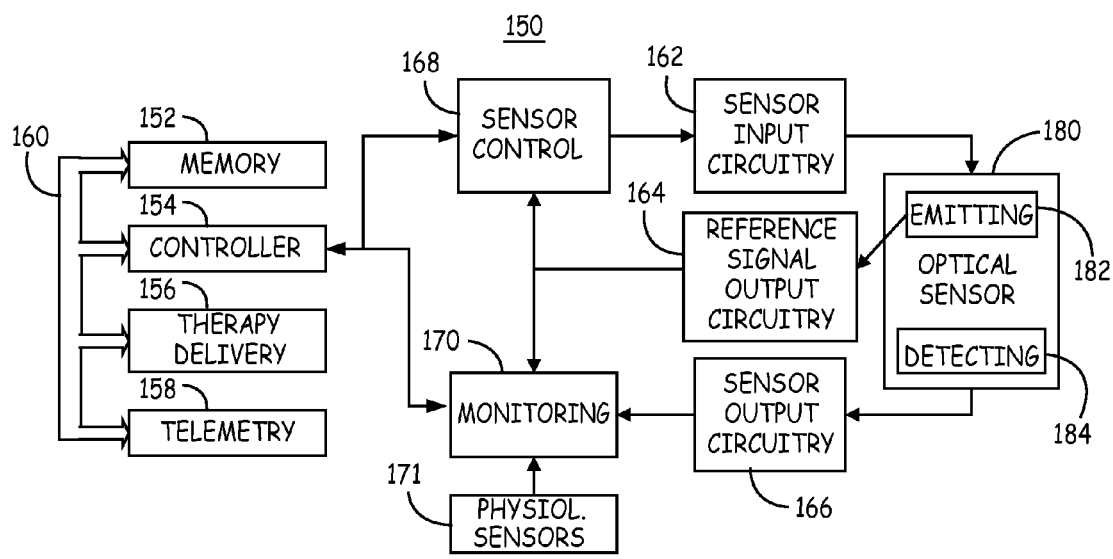
FIG. 3 is a functional block diagram of a medical device system including an optical sensor for monitoring tissue oxygenation.

FIG. 3 is a functional block diagram of a medical device system 150 including an optical sensor 180 for monitoring tissue oxygenation. The functionality described in conjunction with FIG. 3 may be implemented in or distributed across any of the medical device system components shown in FIG. 1. For example, the functionality described in conjunction with FIG. 3 may be implemented in IMD 10, an implantable lead-based sensor 20, an implantable wireless sensor 30, an external wireless sensor 40, or an external sensor in wired communication with an external monitoring device, an external device programmer, or any combination thereof.

Device system 150 includes an optical sensor 180, which may be incorporated along a hermetically sealed housing of a device or carried by a lead. Medical device system 150 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light source for emitting light through a blood perfused tissue of a patient and a light detector for generating a signal representative of an intensity of light emitted and scattered by the blood perfused tissue to the light detector. The light passed into the tissue (including blood) may be selected to include four or more wavelengths for use in computing a measurement correlated to $O_2Sat$, from which an absolute, calibrated tissue $O_2$-Sat may be derived. Typically, the intensity of scattered light falling in the red part of the visible light spectrum and the infrared (IR) portion of the light spectrum is measured.

Absorption of light in the red to infrared spectrum by blood-perfused tissue will vary depending on the presence of chromophores (for example hemoglobin and/or myoglobin) in oxygenated and deoxygenated states present in the measurement volume. The light scattered by blood-perfused tissue and received by the light detector can therefore be used to measure attenuation of light emitted by the sensor due to light absorption (and scattering) by the tissue, which will be correlated to the oxygen available ($O_2Sat$ and HbT) to the tissue. Processing of the optical sensor output signal thus allows tissue oxygen availability to be measured.

Sensor input circuitry 162 is coupled to a light emitting portion 182 of optical sensor 180. Light emitting portion 182 includes one or more light sources for emitting light that, in one embodiment, includes at least four different wavelengths for computing calibrated tissue oxygenation measurements. In alternative embodiments, sensor 180 may be a two-wavelength or three-wavelength sensor used for computing non-calibrated measures of tissue oxygenation. Light sources may emit light at discrete, spaced-apart wavelengths or a single white light source may be used. The measurement of light attenuation for at least four different wavelengths allows a calibrated absolute $O_2Sat$ measurement to be obtained using second derivative methods as will be described herein. Sensor input circuitry 162 provides input signals to the optical sensor 180. In particular, sensor input circuitry 162 provides the drive signals applied to the light source(s) included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Control signals may include a period of no light emission for ambient light measurement. Drive signals may be applied to individual light sources simultaneously to cause "mixed" light emission from all light sources.

In one embodiment, the drive signals are applied sequentially to cause sequential (i.e., non-simultaneous) light emission by individual light sources emitting light at spaced apart wavelengths. In this way, a light detecting portion 184 of sensor 180 will receive scattered light at an individual wavelength at any given time during the operation of sensor 180. It is recognized that referring to an "individual" or "one" wavelength can include a narrow bandwidth of wavelengths approximately centered on, or at least including, the specified individual wavelength emitted by a light source.

The sequential emission of light wavelengths allows multiple light signals to be sequentially measured for each wavelength. A single $O_2Sat$ or HbT measurement will require some minimum interval of time corresponding to the cumulative time durations of each of the separately emitted wavelengths. The time-based sequencing of emitted light may include an interval of no light emission to allow for ambient light measurements and correction of the measured light signals for the presence of ambient light during light emission by the sensor.

In alternative embodiments, the sensor input circuitry 162 is controlled by sensor control module 168 to deliver drive signals simultaneously to each of the light sources at separate, unique frequencies. For example, light sources may be controlled to emit light simultaneously with each individual wavelength having a signature frequency fluctuation. The detecting portion 184 will receive scattered light at all of the wavelengths corresponding to the individual wavelengths simultaneously with each wavelength modulated to a signature frequency. A light detector signal is then demodulated to obtain the individual wavelength signals.

This frequency multiplexing method of controlling the light emitting portion 182 allows simultaneous light emission and detection such that changes in light attenuation by the tissue due to oxygen and hemoglobin changes in the measurement volume can be measured simultaneously for all of the wavelengths rather than at discrete time intervals. This allows for a more instantaneous measurement of $O_2Sat$ and HbT as compared to the sequentially-acquired signals for separate wavelengths in the time-multiplexed method of controlling light emission.

The different wavelengths may be modulated at frequencies that are much greater than the frequency of ambient light changes. Demodulation of the detected light signal will reduce or eliminate effects of ambient light artifact since low frequency components of the detected light signal corresponding to ambient light changes will be substantially removed from the demodulated light detector output signal.

Sensor output circuitry 166 receives the light detector signal from light detecting portion 184 and demodulates, digitizes, filters or performs other appropriate signal conditioning to provide a digital output signal to monitoring module 170. Sensor output circuitry 166 may include an analog-to-digital converter and memory for digitizing an analog output signal from detecting portion 184, providing the digitized signal to monitoring module 170, storing measurement results for future retrieval as well as storing calibration coefficients.

In one embodiment, monitoring module 170 includes processing circuitry that uses the optical signal to compute a volume-independent measurement of $O_2Sat$ and a measurement of HbT (which is both oxygen and volume dependent) using the intensities of the multiple wavelengths measured by detecting portion 184.

As used herein, a "volume-independent" measure of oxygen saturation refers to a measurement that is independent of the size of the optical sensor path that encompasses a measurement volume within a substantially uniform, homogeneous tissue. In other words, in a uniform tissue, a longer optical pathway that encompasses a larger measurement volume and a relatively shorter optical pathway that encompasses a smaller measurement volume within the same uniform tissue will produce substantially equal $O_2Sat$ measurements. A volume-dependent measure of oxygen saturation would be dependent on oxygen and the measurement volume and would thus produce two different measurements for two different measurement volumes in the same uniform tissue. While this volume-independence of the $O_2Sat$ measurement may reduce sensitivity to motion, motion-induced artifact may still be present in the optical signal and the volume-dependent HbT measurements will remain sensitive to motion. Furthermore, in heterogeneous tissue, motion of the sensor may result in different tissue composition within the measurement volume making ambulatory monitoring of tissue oxygenation measurements more challenging.

In some embodiments, a calibrated, absolute $O_2Sat$ and calibrated HbT are derived from the light detector output signal and provided to a device controller 154 (which may include a processor, state machine or other control circuitry) for monitoring tissue oxygenation and controlling device-delivered therapy. In other embodiments, uncalibrated measures of $O_2Sat$ and HbT, indices tissue oxygenation and/or trends of oxygenation measurements are provided to device controller 154.

System 150 is shown to include a therapy delivery module 156. The monitored $O_2Sat$ and HbT may be used in determining when a therapy is needed and in controlling therapy delivery. Therapy delivery module 156 may include electrical pulse generation capabilities for delivering cardiac pacing pulses, cardioversion/defibrillation shocks, or nerve stimulation therapies. Therapy delivery module 156 may additionally or alternatively include a fluid delivery pump for delivering a pharmaceutical or biological fluid to the patient, such as cardiac drugs or other therapeutic fluids.

Device 150 may include other sensors 171 for sensing physiological signals such as ECG or cardiac EGM signals, blood pressure, patient activity, patient posture, heart sounds, temperature, or the like. Such sensor signals may be used in combination with the monitored tissue oxygenation measurements for detecting a patient condition. Other physiological sensors may also be used in triggering the acquisition of tissue oxygenation measurements, adjusting thresholds for detecting insufficient oxygen availability, and establishing different baseline measurements for different patient conditions (e.g., different activity levels, different patient postures, etc.).

In one embodiment, a motion sensor used for detecting patient activity or posture, e.g. an accelerometer, is included to provide a signal corresponding to patient movement. When patient motion is increased due to activity or changes in posture, optical sensor signals may be more susceptible to noise due to motion artifact. A motion sensor may be used to enable noise cancellation circuitry for reducing noise in optical sensor signals.

Data acquired by controller 154 relating to tissue oxygenation measurements may be stored in memory 152 and/or transferred to a medical device programmer, home monitor, computer, or other external or bedside medical device via wireless telemetry module 158 for display and/or review by a clinician. Data relating to tissue oxygenation may also be transmitted to another implantable or external medical device for use in controlling a device delivered therapy. Controller 154 transmits data to and from memory 152, therapy delivery module 156, and telemetry module 158 via data/address bus 160.

As described above, some embodiments include a reference light detector in the light emitting portion 182 of sensor 180. Reference signal output circuitry 164 may then be included for receiving a light detection signal from the reference light detector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of tissue oxygenation measurements computed using stored calibration constants or assuming stable light emission intensity. Accordingly sensor control 168 may include comparators, analog-to-digital convertors, and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. In a four-wavelength sensor, the attenuation at each wavelength is used to compute second derivative attenuation spectra as will be described in greater detail below which enables derivation of a calibrated absolute O₂Sat.

Alternatively, monitoring module 170 uses changes in the emitted light intensity to adjust a computed oxygenation measurement. For example, O₂Sat may be computed assuming a stable emitted light intensity. The actual emitted light intensity may be measured and used to adjust a computed O₂Sat. For example, an initially measured emitted signal intensity and a currently measured emitted signal intensity can be used to adjust or correct an absolute O₂Sat and HbT computed using only the light detector signal from detecting portion 184 and calibration constants.

Figure 4:
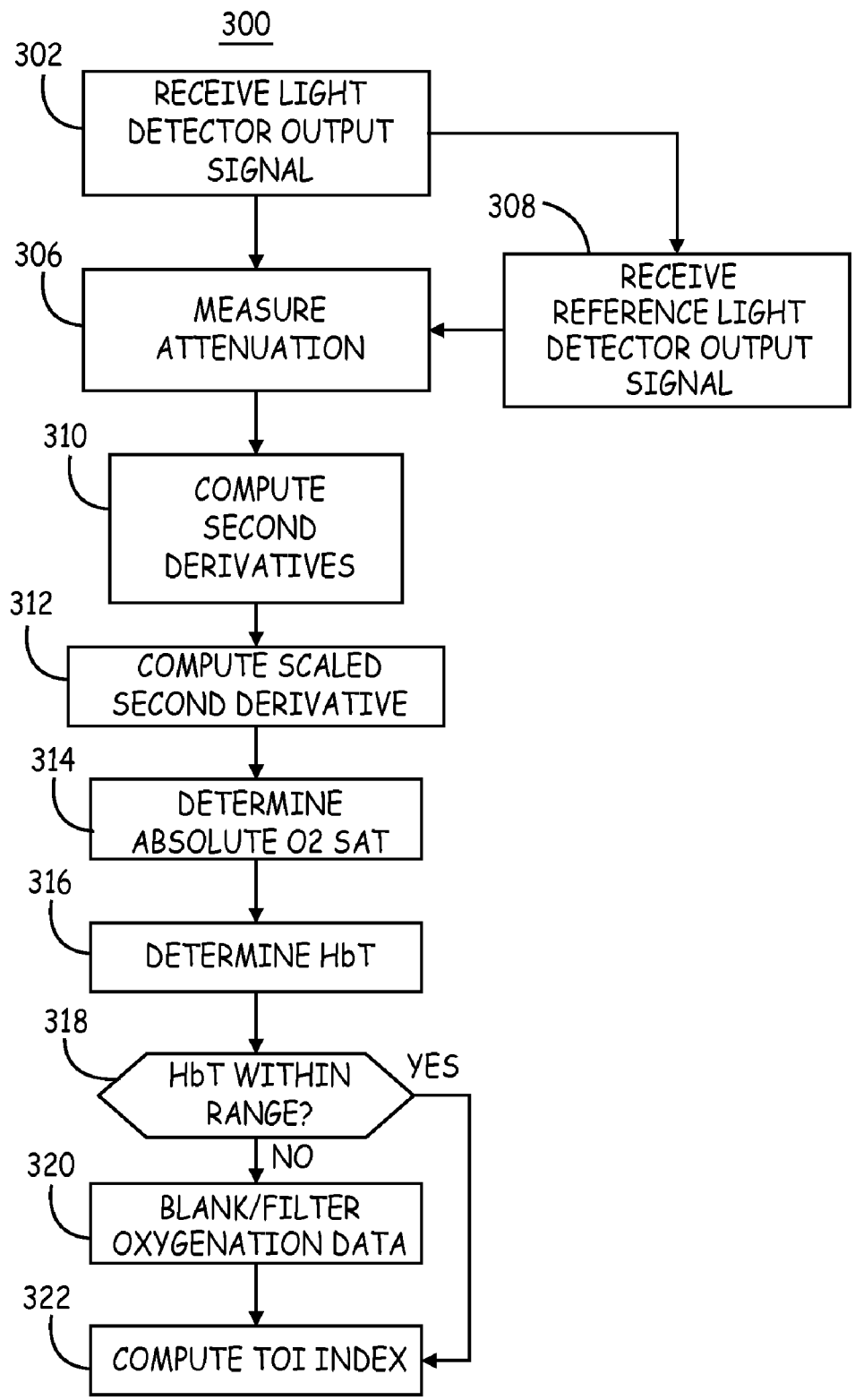
FIG. 4 is a flow chart of a method for operating an optical sensor during tissue oxygenation monitoring.

FIG. 4 is a flow chart of a method 300 for operating an optical sensor during tissue oxygenation monitoring. Flow chart 300 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, the optical sensor is controlled to emit light and the light detector output signal is received from the light detecting portion of the sensor. The light detector output signal may be filtered and corrected for ambient light and baseline offset. If a reference light detector is included in the light emitting portion, the reference light detector may provide an output signal for measuring the light intensity emitted by the sensor at block 308.

At block 306, the attenuation spectrum is measured. In one embodiment, the attenuation of four wavelengths in the red to infrared spectrum is measured. The attenuation of the four different wavelengths may be measured using sequential detection of the different wavelengths by the light detector when a time multiplexed light emission control algorithm is used. Alternatively, measurement of the four different wavelengths may involve demodulation of simultaneously detected light at the four different wavelengths when frequency multiplexed light emission is used. In other embodiments, remitted light from a white light source (or simultaneously emitting separate light sources) may be filtered to obtain the four different wavelength attenuation signals. Remitted light is the light that is scattered by the adjacent tissue volume and received by the optical sensor. The attenuation of remitted light for a given wavelength ($\lambda$) can be measured as the negative logarithm of the ratio of the emitted light intensity ($i_{in}$) to the remitted light intensity ($i_{out}$):

$$A(\lambda) = -\log(i_{in}/i_{out})_\lambda \qquad (1)$$

wherein $i_{in}$ can be measured using the output signal of a reference light detector in the light emitting portion of the sensor, and $i_{out}$ is measured using the output signal of the light detecting portion for a given wavelength. The term "attenuation measurement" as used herein generally refers to a measure of the attenuation of light due to absorption and scattering by tissue along the optical path of the sensor. The measured attenuation may not be an exact measurement of the actual light absorption by the tissue volume since light reflections and scattering may cause attenuation of the remitted light intensity not attributed to actual light absorption by the tissue.

In alternative embodiments, the emitted intensity for each wavelength $i_{in}$ in Equation (1) is assumed constant and is optionally measured prior to implantation, e.g., at the time of manufacture, and assumed to be sufficiently stable throughout the usable life of the sensor and not cause significant measurement error. In this case, a reference light detector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the light source(s).

The attenuation for four wavelengths is determined to allow the second derivative with respect to wavelength of the attenuation spectra at two intermediate wavelengths to be computed. This determination of second derivatives at two intermediate wavelengths allows for computation of a scaled second derivative, which is a ratio of the two second derivatives. By properly selecting the intermediate wavelengths, a scaled second derivative is an oxygen-dependent and volume-independent ratio and therefore provides a measure of $O_2Sat$. At block 310, the attenuation measurement for two wavelengths intermediate the four detected wavelengths is converted to a second derivative (D"), expressed generally as:

$$D''(\lambda_i) = A(\lambda_{i+1}) - 2A(\lambda_i) + A(\lambda_{i-1}) \quad (2)$$

wherein $A(\lambda_i)$ is the light attenuation, measured according to Equation 1 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths. Equation 2 assumes equal spacings between the four wavelengths. When unequal spacings are used, a different equation for the second derivative with respect to wavelength is required to account for the different wavelength spacings by retaining the differences between wavelengths in denominators of the first and second derivative equations.

The second derivative of a selected intermediate wavelength is scaled by another computed second derivative at block 312. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD") of the 720 nm attenuation can be expressed as the following ratio:

$$SD'' = D''(720)/D''(760) \quad (3)$$

This SD"(720) is dependent on oxygen saturation of the hemoglobin present in the measurement volume but substantially independent of the size of the measurement volume (assuming a uniform tissue), defined by the optical path of the sensor. Thus, measuring attenuation for at least four wavelengths allows the second derivatives of two intermediate wavelengths to be computed, allowing computation of a measurement volume-independent, scaled second derivative.

The optical sensor may be calibrated at the time of device manufacture using control samples, for example in an in vitro blood circuit, having known oxygen saturation and total hemoglobin concentration. The calibration process may generate a look-up table relating second derivatives computed from the light detector output signal and the known $O_2Sat$ and HbT. The look-up table is stored in the device memory. The look-up table can then be used to derive absolute calibrated $O_2Sat$ and Hbt values from an optical sensor measurement.

Alternatively, calibration methods may include curve-fitting methods to solve for coefficients defining best-fit curves to the calibration data. In one embodiment, the absolute tissue oxygen saturation is defined by:

$$O_2 \text{sat} = Ae^{B(SD''(\lambda_i))} + C \quad (4)$$

wherein SD" is a scaled second derivative of the attenuation spectra at a selected intermediate wavelength ($\lambda_i$). By properly selecting the wavelength $\lambda_i$ and the other wavelength used for scaling, the scaled second derivative is an oxygen-dependent and volume-independent ratio. The coefficients A, B and C are determined through best-fit analysis of measurements of the scaled second derivative for calibration samples having known oxygen saturation.

The total tissue hemoglobin volume fraction can be defined by the equation:

$$HbT = [M(100 - O_2\text{Sat})^N + L] * [(D''(\lambda i)/SF] \quad (5)$$

wherein M, N, and L are coefficients determined during calibration and $D''(\lambda_i)$ is the second derivative of the attenuation spectra with respect to wavelength at the selected intermediate wavelength $\lambda_i$. $D''(\lambda)$ is measured for samples containing known total hemoglobin volume fraction and known oxygen saturation. The calibration coefficients M, N and L may then be computed for a best-fit of the measured second derivative values and known $O_2Sat$ and HbT. Alternatively, the measured second derivative values and known $O_2Sat$ and HbT may be used to generate a look-up table for converting the measured second derivative values to HbT.

SF is a spacing factor which may be used to adjust for an emitting-to-detecting portion spacing that may be different during tissue measurements than that used during calibration. Since the HbT measurement is dependent on both $O_2Sat$ and the measurement volume, and measurement volume is dependent on the optical path of the sensor, defined at least in part by the spacing between the emitting and detecting portions, the HbT measurement needs to be corrected for changes in emitting-to-detecting portion spacing. For example, the sensor may be calibrated using a nominal emitting-to-detecting portion spacing, however when multiple emitting and/or detecting portions are selectable in a sensor or combination of sensors, the spacing may be different during monitoring than that used during calibration. As such, a spacing factor corresponding to selectable emitting-to-detecting portion spacings may be stored and used to correct the HbT measurement when a different spacing is used during monitoring than during calibration.

Once the scaled second derivative is obtained, the stored calibration data is used at block 314 to derive the absolute $O_2Sat$. The second derivative for attenuation at 720 nm wavelength (and 760 nm) is dependent on oxygen saturation and total hemoglobin. Thus, at block 316, HbT may be determined knowing the D"(720) (or D"(760)) with respect to wavelength, the derived absolute $O_2Sat$, and the stored calibration data.

Tissue oxygenation, or the availability of oxygen to tissue, as defined herein, is a function of both tissue $O_2Sat$ and HbT. Depending on the particular tissue oxygenation monitoring application, the derived $O_2Sat$ and HbT may each be used separately in a monitoring algorithm or combined to determine a tissue oxygenation index used to monitor a patient's status and/or control a therapy. At block 322, a tissue oxygenation index may be computed as a function of $O_2Sat$ and HbT. For example, a tissue oxygenation index (TOI) may be a weighted combination of the $O_2Sat$ and HbT measurements. In one embodiment, a tissue oxygenation index is computed as:

$$TOI = W_1 O_2\text{Sat} + W_2 HbT \quad (6)$$

wherein $W_1$ and $W_2$ are weighting factors selected for a particular application. may be tailored to an individual patient. It is contemplated that non-linear combinations of $O_2Sat$ and HbT may also be used.

A tissue oxygenation index computed using absolute measurements of $O_2Sat$ and HbT can be available on a continuous or periodic basis. The TOI and/or the individual calibrated values of $O_2$ Sat and HbT may be used for tracking a patient's tissue oxygenation and changes in patient status based on changes in oxygenation.

The absolute values of $O_2Sat$, HbT and the TOI computed using the calibrated absolute values of $O_2Sat$ and HbT are computed and stored. Additionally, differences between each of these oxygenation measures and a baseline or other earlier corresponding measure may be computed and stored as calibrated trended variables. As such, in addition to storing the absolute values, trended values of each of the oxygenation measurements may be stored as changes in the absolute values over time, referred to as $dO_2$ Sat, dHbT or dTOI, which each represent the difference between a current measurement and a previous measurement of the same calibrated measurement.

Alternatively or additionally, non-calibrated values and trends of the oxygenation measurements may be determined and stored. Since sensor calibration can be time consuming and computing a calibrated measurement adds to computational burden of the device, it may be desirable to compute non-calibrated values and trends of oxygenation measurements without conversion of those measurements to an absolute value. For example, a scaled second derivative of a properly selected wavelength, $SD''(\lambda)$, is a volume-independent measure of $O_2Sat$ and may be determined as an index of $O_2Sat$ without conversion to a calibrated measurement. Likewise, $D''(\lambda)$, which is volume and oxygen dependent, can provide an index of HbT without conversion to a calibrated measurement. Each of these uncalibrated tissue oxygenation measurements may be used individually as baseline indices of tissue oxygenation or combined in a computation of a TOI, such as a weighted linear combination of the uncalibrated measurements similar to Equation (4) above. The uncalibrated measure of $SD''(\lambda)$ used as an $O_2Sat$ index is a volume-independent measurement which can provide meaningful measurements at a single time point, or over long- or short-term trends.

The uncalibrated measurements of $SD''(\lambda)$, $D''(\lambda)$, and a TOI computed using $SD''(\lambda)$ and $D''(\lambda)$ may be determined and stored for use as baseline measurements and measured at future time points for monitoring patient status and for use in detecting physiological events and controlling device-delivered therapies. Trends in each of the uncalibrated measurements over time, referred to as $dSD''(\lambda)$, $dD''(\lambda)$, and dTOI, may also be determined and stored as the difference between a current uncalibrated measurement and a previous corresponding measurement. In summary, various algorithms for monitoring tissue oxygenation may utilize calibrated measurements ($O_2Sat$ and HbT), trends in the calibrated measurements ($dO_2Sat$ and dHbt), uncalibrated measurements ($SD''(\lambda)$ and $D''(\lambda)$), trends in the uncalibrated measurements ($dSD''(\lambda)$ and $dD''(\lambda)$) or any combination of the foregoing measurements and trends. Furthermore, indices determined using 2- or 3-wavelength sensors may be used.

The oxygen saturation measurement derived from a scaled second derivative is a volume-independent measurement and is therefore expected to have reduced susceptibility to motion artifact, which could alter the optical path of the sensor and thus alter the measurement volume. However, some embodiments may utilize the measured HbT, which is dependent on the measurement volume, to filter or blank tissue oxygenation monitoring during periods in which HbT is out of a normal range, which may be due to motion or activity of the patient.

Accordingly, in one embodiment, the measured HbT is compared to an acceptable range, e.g. between approximately 1% and approximately 25%, at block 318. If HbT is out of the acceptable range, tissue motion may be causing erroneous HbT measurements. At block 320, the tissue oxygenation measurement is blanked or otherwise deemed invalid based on the out-of-range HbT measurement. For example, patient activity may result in oscillatory movements that produce a signal that is intermittently in and out of the acceptable range. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored.

Alternatively, $O_2Sat$ and HbT measurements may be filtered based on the fluctuation of HbT. If HbT variability is low, than a low rate of averaging (low pass filtering) $O_2Sat$ and HbT measurements may be used. If HbT variability increases, an increasing filtering or averaging frequency may be used based on the increased HbT variability.

The optical sensor signal susceptibility to motion artifact may vary depending on the location of the sensor on the patient's body, the characteristics of the tissue adjacent the sensor (thickness and uniformity relative to the measurement volume of the optical sensor) and patient-related conditions (activity, posture, etc.). Accordingly, cancellation of noise present in the optical sensor signal due to motion or other noise sources may be needed to provide reliable oxygenation measurements.

Figure 5:
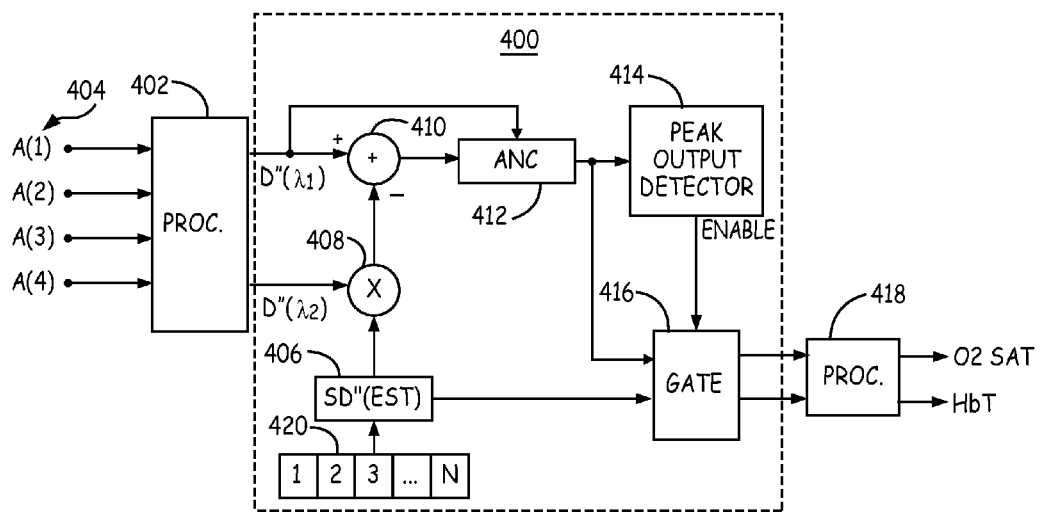
FIG. 5 is a functional block diagram of noise cancellation circuitry that may be used in conjunction with an optical sensor for monitoring tissue oxygenation.

FIG. 5 is a functional block diagram of noise cancellation circuitry 400 that may be used in conjunction with an optical sensor for monitoring tissue oxygenation. Noise cancellation circuitry 400 is used to at least partially remove noise from an optical sensor signal used to determine tissue oxygenation. A processor 402 receives light attenuation signals 404, each corresponding to a different wavelength, from the output circuitry of an optical sensor. From the attenuation spectrum, processor 402 computes two second derivatives $D''(\lambda_1)$ and $D''(\lambda_2)$ of the light attenuation spectrum with respect to wavelength at two different, spaced apart wavelengths. In one embodiment, processor 402 receives at least four attenuation signals A(1) through A(4) for computing second derivatives at approximately 720 nm and 760 nm as described above, though other wavelengths may be used. The two second derivatives of light attenuation could be used to compute $O_2Sat$ and Hbt directly. However, in the illustrative embodiment, $D''(\lambda_1)$ and $D''(\lambda_2)$, are first provided as input to noise cancellation circuitry 400 to remove noise from the $D''(\lambda_1)$ and $D''(\lambda_2)$ signals prior to computing oxygenation measurements.

Since noise artifact may be of high frequency and highly variable, the attenuation signals 404 for different wavelengths may be received simultaneously such that each signal 404 is similarly influenced by motion or other sources of noise. If not received simultaneously, e.g. if attenuation signals are measured sequentially in a time-multiplexed manner as described above, the input attenuation signals 404 may be provided at a high sampling frequency (i.e., high rate sequencing of attenuation measurements) to minimize changes in noise signal correlation across different wavelengths.

Noise cancellation circuitry 400 includes an estimated value generator 406 which stores or determines guessed or estimated values of a ratio, SD"(EST), of the two second derivatives $D''(\lambda_1)$ and $D''(\lambda_2)$. An initial guessed or estimated value may correspond to a previously measured value or may be set at a default value.

A multiplier 408 receives the guessed value of SD" from value generator 406 and the measured second derivative $D''(\lambda_2)$ from processor 401, used in the denominator of a second derivative ratio. Multiplier 408 multiplies the guessed SD" value with the measured $D''(\lambda_2)$ to provide an estimate of $D''(\lambda_1)$.

The output of multiplier 408 is provided as a negative input to a summation operator 410 and is summed with the measured $D''(\lambda_1)$ input to provide an estimate of noise. The output of summation operator 410 is provided to an adaptive noise canceller 412. Adaptive noise canceller receives the measured $D''(\lambda_1)$ signal and subtracts the output of the summation operator 410 (the estimated noise) from the measured $D''(\lambda_1)$ signal.

The output power of the adaptive noise canceller (ANC) 412 will be maximized when the guessed SD" value is the correct value. When the correct SD" value is guessed, the output of the multiplier 408 includes the correct $D''(\lambda_1)$ value plus noise. When the correct $D''(\lambda_1)$ value (with noise) is provided as negative input to summation operator 410, the output of the summation operator 410 will be a reference noise signal with the $D''(\lambda_1)$ signal removed since noise on the actual $D''(\lambda_1)$ signal and the estimated $D''(\lambda_1)$ signal will be different in amplitude but correlated. The output of the summation operator 410 thus provides a reference noise signal that can be adaptively removed from the measured $D''(\lambda_1)$ signal by adaptive noise canceller 412. Thus, when the guessed value of SD" contains the actual $D''(\lambda_1)$ signal (with correlated noise), output power of ANC 412 will be maximized. The output of ANC 412 will be the actual $D''(\lambda_1)$ signal with noise removed or significantly reduced.

When the guessed value of SD" is incorrect, the reference noise signal provided as output from summation operator 410 will still include the $D''(\lambda_1)$ signal which will then be removed from the measured $D''(\lambda_1)$ by ANC 412. The output power of ANC 412 will be relatively lower when the incorrect guessed value SD"(EST) is provided as input to multiplier 408.

The output power of ANC 412 is monitored by peak output detector 414 while different guessed values for SD"(EST) are provided as input to multiplier 408. Guessed values may be provided in increments over a possible measurement range or in a binary search or other selected search algorithm.

In one embodiment, guessed values are selected from two or more bins 420. Bins 420 are defined as ranges of possible SD" values. Multiple bins 420 may be provided having equal or unequal bin widths (ranges). A median value within each bin may be generated as a guess of the actual SD" value. For example, two bins may be defined, one greater than a hypoxia detection threshold and one less than a hypoxia detection threshold. In another example, three bins for SD" values may be defined corresponding to low, normal, and high ranges of $O_2$Sat. The guessed bin value resulting in the greatest output power of ANC 412 corresponds to the bin containing the correctly guessed, actual SD" value.

In this way, a bin corresponding to suprathreshold or sub-threshold $O_2$Sat may be identified for detecting hypoxia. Alternatively, a bin corresponding to a low, normal or high $O_2$Sat may be identified. Identifying a bin containing the correct guess of SD" can be used for determining a tissue oxygenation, e.g. as hypoxic or not hypoxic, or as high, normal or low, without additional computations of an absolute calibrated value of $O_2$Sat.

Peak output detector 414 identifies the peak output power of ANC 412 as guessed SD" values are generated so that the guessed value that contains the $D''(\lambda_1)$ signal can be identified. Gate 416 may buffer guessed SD" values (or bin identities) and the ANC output signal until peak output power is identified. Peak output detector 414 may provide a signal to gate 416 to pass the correctly guessed SD" value (or corresponding bin) to processor 418 when the peak output power is identified. The noise corrected $D''(\lambda_1)$ signal output of ANC 412 may also be passed to processor 418 by gate 416 when the peak output detector 414 identifies a peak output power of ANC 412.

Processor 418 may determine a tissue oxygenation based on the correctly guessed, actual SD" value. In one embodiment, the tissue oxygenation may be determined as hypoxic or not hypoxic based on determining if the highest ANC output power corresponds to a guessed SD" value falling respectively below or above a hypoxia detection threshold. In another embodiment, the processor 418 may determine the tissue oxygenation as low, normal or high based on a guessed SD" value resulting in the highest ANC output power falling in a respective low, normal or high bin.

Alternatively or additionally, processor 418 may compute absolute calibrated values of $O_2$Sat and HbT. $O_2$Sat may be computed using the actual SD" value (the guessed value associated with maximum ANC output power) and previously stored calibration data. HbT may then be computed using the computed $O_2$Sat and the output signal of ANC 412 when the peak output power is identified. The output signal will correspond to the measured $D''(\lambda_1)$ signal with the reference noise signal removed and will thus be a noise-corrected signal. As such, noise corrected, absolute calibrated values of $O_2$Sat and HbT can be computed. Alternatively, a tissue oxygenation index may be computed using the actual SD" value, the noise-corrected $D''(\lambda_1)$ signal output of ANC 412, or a combination of both.

The noise cancellation circuitry described herein is not limited to use with optical sensors providing attenuation measurements at four different wavelengths. In alternative embodiments, optical sensor systems providing attenuation measurements used to compute any ratio of attenuation measurements at two different wavelengths may be implemented in conjunction with noise cancellation circuitry 400. The attenuation of a first wavelength, or a derivative or other measurement thereof, and the attenuation of a second wavelength, or a derivative or other measurement thereof, may be provided as input to noise cancellation circuitry 400. A guessed ratio of the first and second attenuation measurements may then be generated by estimated value generator 406.

Figure 6:
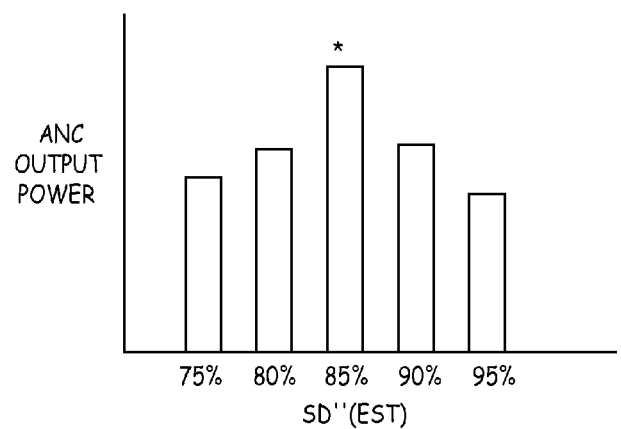
FIG. 6 is a graphical view of an adaptive noise canceller output power as a function of an estimated ratio of second derivatives of light attenuation.

FIG. 6 is a graphical view of an ANC output power as a function of a guessed SD" value (SD"(EST)) corresponding to different calibrated values of $O_2$Sat (75% through 95%). The maximum ANC output power (indicated by an asterisk) occurs when the guessed value of SD" corresponds to an 85% $O_2$Sat. As such, this guessed value of SD" may be provided to a processor for computing the calibrated value of $O_2$Sat, HbT and/or identify the bin containing the guessed SD" value corresponding to maximum ANC output power.

Figure 7:
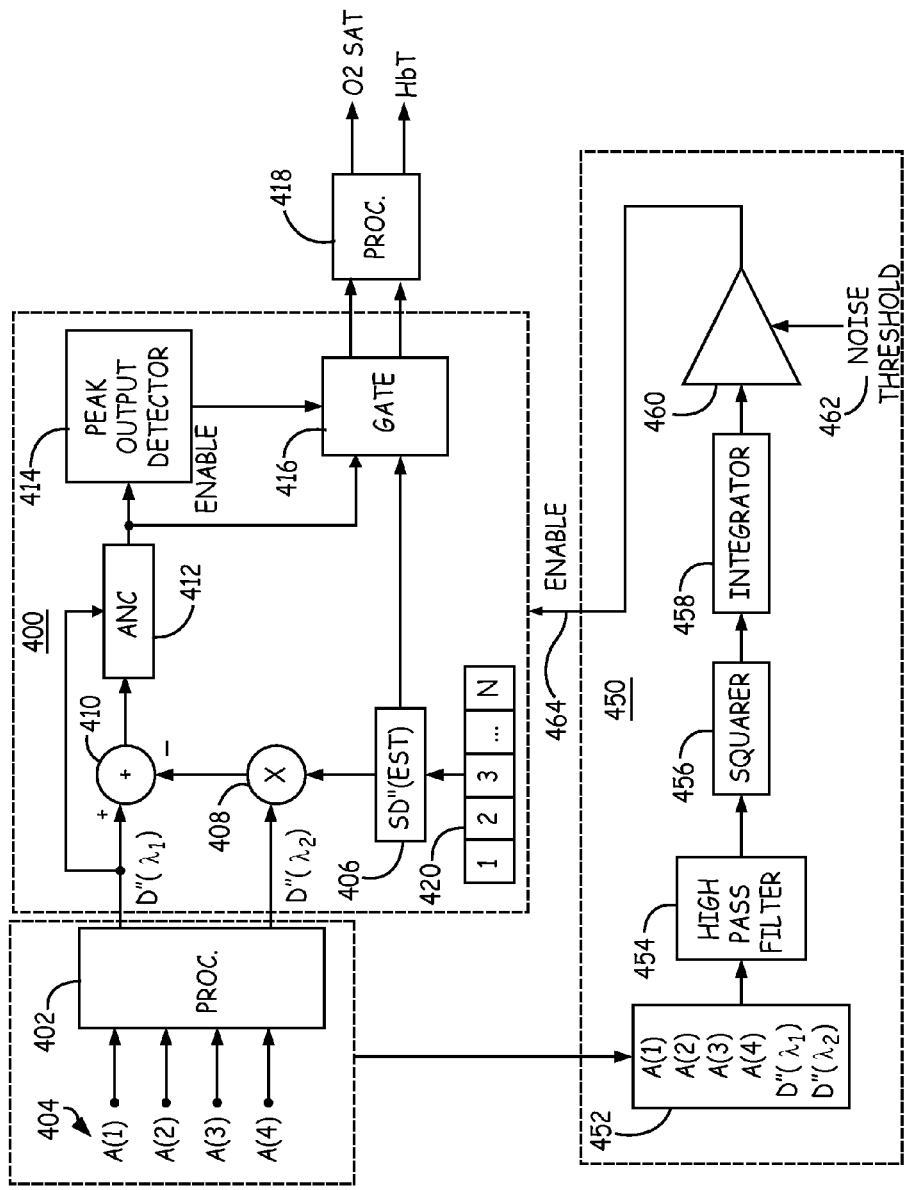
FIG. 7 is a functional block diagram of an alternative embodiment of noise cancellation circuitry used in conjunction with an optical sensor.

FIG. 7 is a functional block diagram of an alternative embodiment of noise cancellation circuitry used in conjunction with an optical sensor. The same reference numbers are used in FIG. 7 to identify identical elements shown in FIG. 5. Noise cancellation circuitry may be selectively enabled when the optical sensor signals are determined to be noise contaminated or having increased susceptibility to noise. Noise detection circuitry 450 may be provided to enable operation of noise cancellation circuitry 400 when noise is detected or suspected.

In general, noise detection circuitry 450 provides an enable signal 464 in response to detecting a high level of noise in the optical sensor signals or detecting conditions that likely increase the optical sensor signal susceptibility to noise. In various embodiments, noise detection circuitry 450 may utilize a number of methods for detecting the presence of noise or an increased susceptibility to noise. Such methods may include using another sensor signal or monitoring variability in computed oxygenation measurements.

Other sensor signals that may be monitored to detect a likelihood of increased optical sensor signal noise include a patient activity sensor and a patient posture sensor. Increased patient activity and/or a change in posture may increase motion artifact in the optical sensor signal. As such, noise cancellation circuitry 400 may be enabled or disabled based on detecting respectively high or low noise conditions using a motion sensor capable of detecting patient activity and/or posture.

The variability of oxygenation measurements may also be an indicator of increased noise artifact. For example, when high variability of $O_2Sat$ and/or HbT is detected when noise cancellation circuitry is not operating, the noise cancellation circuitry may be enabled.

In the embodiment shown in FIG. 7, noise detection circuitry 450 monitors the optical sensor signals for noise content. Noise detection circuitry 450 includes a signal input 452 which may include the optical sensor attenuation signal 404 for one or more wavelengths (A(1) through A(4)), a processor derived second derivative $D''(\lambda_1)$ or $D''(\lambda_2)$, or any combination of these signals.

The signal input 452 is provided to a high pass filter 454. The frequency characteristics of high pass filter 454 may be selected according to a particular sensing application and may generally be provided to pass frequencies greater than a physiological rate of change expected in tissue oxygenation. In one embodiment, the filter 454 is provided with a high-pass corner between approximately 0.1 Hz and approximately 10 Hz, without limitation. A high pass corner may be selected to remove frequencies associated with other physiological motion such as blood pulsatility (e.g. up to 150 bpm) or respiration (e.g. approximately 12 breaths per minute).

The high pass filter output is provided as input to a squarer 456, which serves to rectify and amplify the high pass filtered signal. The output of squarer 456 is provided as input to an integrator 458. Integrator 458 provides a noise measurement corresponding to the high frequency content or AC power of the signal input 452. Integrator 458 may integrate the rectified signal for a predetermined interval of time to obtain a noise measurement. The output of integrator 458 is provided to a comparator 460 which compares the noise measurement to a predefined noise threshold 462.

If the noise threshold 462 is exceeded, an enable signal 464 is provided to enable noise cancellation circuitry 400 to operate. When noise cancellation circuitry is not operating, processor 418 may use the $D''(\lambda_1)$ and $D''(\lambda_2)$ signals measured from the input attenuation signals 404 directly for computing an oxygenation measurement. While processor 418 and processor 402 are shown as two distinct processing units, it is recognized that signal processing methods may be implemented in a single processor.

Figure 8:
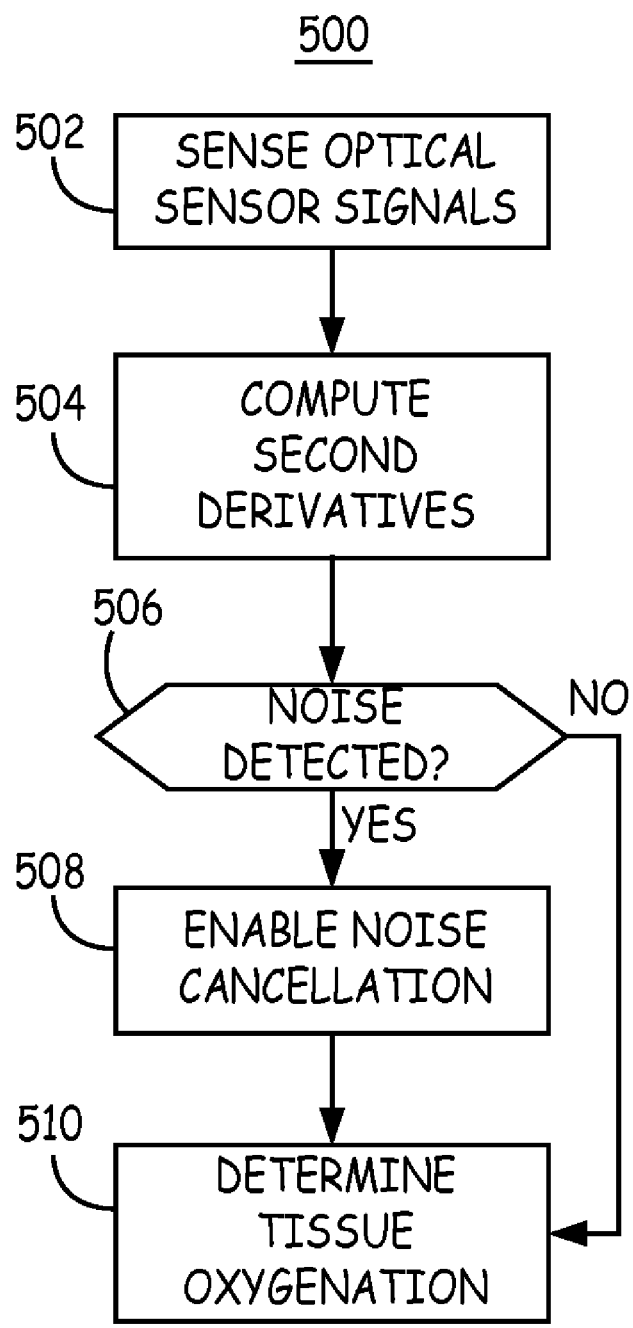
FIG. 8 is a flow chart of a method for cancelling noise in an optical sensor signal.

FIG. 8 is a flow chart of a method 500 for cancelling noise in an optical sensor signal. At block 502, an optical sensor signal is sensed, and attenuation signals for at least four wavelengths are used to compute two second derivatives at two different spaced apart wavelengths at block 504.

At block 506, a noise detection algorithm is performed. Noise detection performed at block 506 may correspond to the noise detection method described in conjunction with FIG. 7, use other sensor signals such as a motion sensor signal as described previously, or monitor oxygenation measurement variability. If no noise is detected, a tissue oxygenation measurement is computed at block 510 using the optical sensor signal without noise correction.

If noise is detected at block 506, noise cancellation circuitry 400 as shown in FIGS. 5 and 7 is enabled. The output of noise cancellation circuitry is used for determining tissue oxygenation at block 510. The output of noise cancellation circuitry may include an actual ratio of input signals that results in a maximum ANC output power. The output of noise cancellation circuitry may additionally or alternatively include a noise-corrected optical sensor signal corresponding to a maximum output power of the ANC. The actual ratio, which is the guessed ratio value that results in a maximum ANC output power, may be used to compute a calibrated absolute value of a tissue oxygenation measurement or identify a bin containing the actual ratio. The absolute value or an identified bin may then be compared to one or more thresholds or ranges to determine a relative oxygenation status of the tissue (e.g. high, low or normal).

The determined tissue oxygenation, which may be a calibrated absolute value, an indexed value, a bin identity, or a relative oxygenation status determined based on a determined actual ratio, may then be used by a medical device in monitoring the patient, controlling a therapy, displaying an oxygenation status to the patient or clinician, or generating a warning or notification to the patient or clinician that low tissue oxygenation is detected.

In some embodiments, noise cancellation circuitry is always enabled when optical sensor signals are being processed to allow identification of a bin relative to a detection threshold to be identified quickly based on a minimum of two guessed ratio values. If a subthreshold bin is identified, tissue hypoxia may be immediately detected and responded to without computing calibrated values of oxygenation measurements.

Figure 9:
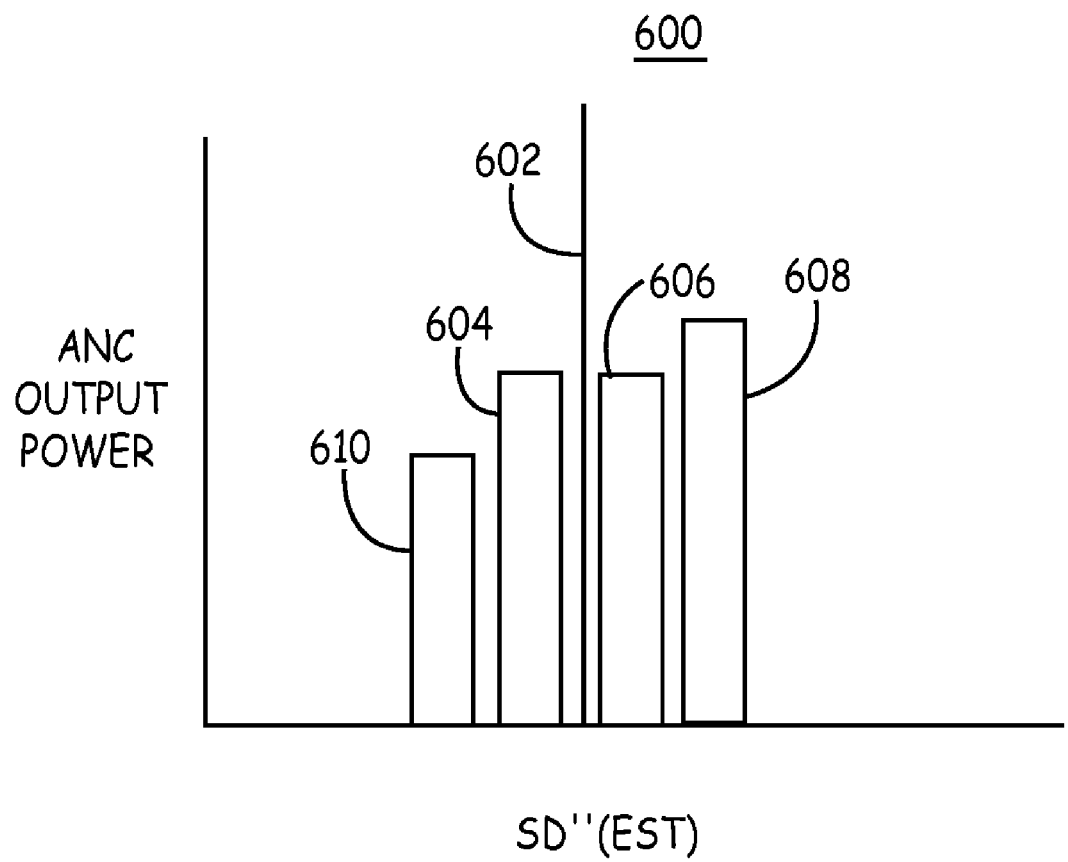
FIG. 9 is a graphical depiction of identification of a bin containing an actual ratio of second derivatives of light attenuation.

FIG. 9 is a graphical depiction 600 of identification of a bin containing a guessed SD" resulting in a peak ANC output power. A threshold 602 may be defined for detecting a tissue oxygenation condition, such as a threshold for detecting hypoxia. Initially, two values for SD" (EST) are tested corresponding to midpoints of a subthreshold bin 604 and a suprathreshold bin 606. The ANC output power is approximately equal for the two bins making discernment of the bin location of the actual SD" unclear. When two guessed values are tested with similar ANC output power, a third guessed value, greater than, less than, or intermediate to the original guessed values may be tested.

In the example shown in FIG. 9, a third guessed value corresponding to a second subthreshold bin 610 results in an ANC output power lower than the ANC output power for the initial two guesses. This result indicates that the probability that an actual SD" associated with a peak ANC output power is in a subthreshold bin is low and the probability that the actual SD" is in a suprathreshold bin is high. The output power is increasing as SD" guessed values are increasing. As such, an immediate determination may be made that the tissue oxygenation is above threshold 602 without determining the actual SD". If threshold 602 is a hypoxia detection threshold, no hypoxia is detected.

Alternatively or additionally, a guessed value corresponding to a second suprathreshold bin 608 is tested. In the example shown, the guessed value for bin 608 results in a relative peak output power for the bin values tested. This result confirms with high probability that the actual SD" is a suprathreshold value. In this way, bin values may be tested to quickly identify a tissue oxygenation relative to a threshold or oxygenation status range in place of computing absolute calibrated tissue oxygenation measurements, or even determining the actual SD" associated with a maximum peak ANC output power. The probable SD" location relative to a threshold can be used for detecting a patient condition or managing a therapy.

Thus, a medical device and methods for use have been presented in the foregoing description with reference to specific embodiments. It is appreciated that various modifications to the referenced embodiments may be made without departing from the scope of the disclosure as set forth in the following claims.

The invention claimed is:

1. A medical device system, comprising:
   an optical sensor for producing a signal corresponding to tissue light attenuation;
   a processor receiving the optical sensor signal and configured to compute a first measure of light attenuation at a first light wavelength and a second measure of light attenuation at a second light wavelength; and
   noise cancellation circuitry for receiving the first measure and the second measure and generating an estimated ratio of the first and second measures, the noise cancellation circuitry providing a peak output power when the guessed ratio corresponds to an actual ratio containing the first measure;
   the processor determining a tissue oxygenation using the estimated ratio corresponding to the peak output power of the noise cancellation circuitry.

2. The system of claim 1, wherein the optical sensor produces a signal corresponding to tissue light attenuation for at least four wavelengths, and
   the processor being configured to compute the first measure as a second derivative of light attenuation with respect to a first light wavelength and the second measure as a second derivative of light attenuation with respect to a second light wavelength.

3. The system of claim 1, further comprising a memory to store calibration data relating values of the ratio to tissue oxygen saturation, wherein the processor is configured to compute an absolute tissue oxygen saturation using the estimated ratio corresponding to the peak output power of the noise cancellation circuitry and the calibration data.

4. The system of claim 1, wherein the processor is configured to compute a measure of tissue oxygen saturation using the estimated ratio and compute a measure of total hemoglobin volume fraction using the computed tissue oxygen saturation and a noise cancellation circuitry output signal corresponding to a peak output power.

5. The system of claim 1, further comprising a memory to store a plurality of bins, each bin of the plurality of bins defining a range of possible values for the ratio, wherein the processor is configured to determine the tissue oxygenation by identifying one of the plurality of bins associated with a peak output power of the noise cancellation circuitry.

6. The system of claim 5, wherein determining the tissue oxygenation comprises detecting hypoxia in response to identifying the one of the plurality of bins.

7. The system of claim 1, wherein the noise cancellation circuitry is configured to generate estimated values for the ratio in a binary search mode.

8. The system of claim 1, further comprising a noise detector generating an enable signal for enabling the noise cancellation circuitry.

9. The system of claim 8, further comprising a motion sensor coupled to the noise detector, the noise detector generating the enable signal in response to the motion sensor.

10. The system of claim 8, wherein the noise detector determines a noise measurement of a high frequency content of the optical sensor signal and enables the noise cancellation circuitry in response to the determined noise measurement.

11. The system of claim 8, wherein the noise detector determines a variability of an oxygenation measurement.

12. The system of claim 1, further comprising an adaptive noise canceller receiving the first measure and a reference noise signal to produce the peak output power.

13. The system of claim 11, further comprising circuitry for generating the reference noise signal using the estimated ratio, the first measure, and the second measure.

14. A method, comprising;
   sensing an optical signal corresponding to tissue light attenuation;
   computing a first measure of light attenuation at a first light wavelength and a second measure of light attenuation at a second light wavelength using the sensed optical signal;
   generating an estimated ratio of the first and second measures;
   determining a reference noise signal using the estimated ratio, the first measure and the second measure;
   providing the reference noise signal and the first measure to an adaptive noise canceller;
   determining an actual ratio of the first and second measures as an estimated ratio corresponding to a peak output power of the adaptive noise canceller; and
   determining a tissue oxygenation using the actual ratio.

15. The method of claim 14, wherein sensing the optical signal comprises sensing a signal corresponding to tissue light attenuation for at least four wavelengths, computing the first measure comprises computing a second derivative of light attenuation with respect to a first light wavelength, and computing the second measure comprises computing a second derivative of light attenuation with respect to a second light wavelength.

16. The method of claim 14, further comprising storing calibration data relating values of the ratio to tissue oxygen saturation and computing an absolute tissue oxygen saturation using the actual ratio.

17. The method of claim 14, wherein determining a tissue oxygenation comprises:
   computing a measure of tissue oxygen saturation using the actual ratio; and
   computing a measure of total hemoglobin volume fraction using the computed tissue oxygen saturation and an output signal of the adaptive noise canceller corresponding to a peak output power.

18. The method of claim 14, further comprising storing a plurality of bins, each bin of the plurality of bins defining a range of possible values for the ratio, and wherein determining the tissue oxygenation comprises identifying one of the plurality of bins associated with a peak output power of the adaptive noise canceller.

19. The method of claim 18, wherein determining the tissue oxygenation comprises detecting hypoxia in response to identifying the one of the plurality of bins.

20. The method of claim 14, wherein generating an estimated value for the ratio comprises generating estimated values in a binary search mode.

21. The method of claim 14, further comprising generating an enable signal for enabling the noise cancellation circuitry.

22. The method of claim 21, further comprising:
   sensing a motion sensor signal; and
   generating the enable signal in response to the motion sensor signal.

23. The method of claim 21, further comprising:
   determining a noise measurement of a high frequency content of the optical sensor signal; and
   generating the enable signal in response to the determined noise measurement.

24. The method of claim 21, further comprising:
   determining a variability of an oxygenation measurement; and
   generating the enable signal in response to the variability.

25. A non-transitory computer readable medium having computer executable instructions for performing a method comprising:

sensing an optical signal corresponding to tissue light attenuation;

computing a first measure of light attenuation at a first light wavelength and a second measure of light attenuation at a second light wavelength using the sensed optical signal;

generating an estimated ratio of the first and second measures;

determining a reference noise signal using the estimated ratio, the first measure and the second measure;

providing the reference noise signal and the first measure to an adaptive noise canceller;

determining an actual ratio of the first and second measures as an estimated ratio corresponding to a peak output power of the adaptive noise canceller; and determining a tissue oxygenation using the actual ratio.

* * * * *